United States Patent
Boyle et al.

(10) Patent No.: US 11,771,457 B2
(45) Date of Patent: *Oct. 3, 2023

(54) SCORING BALLOON WITH TRANSLATING SCORING WIRES

(71) Applicant: C.R. Bard, Inc., Tempe, AZ (US)

(72) Inventors: Melissa Boyle, Phoenix, AZ (US);
Corey Rousu, Glendale, CA (US);
Mark Nicholas Wright, Gilbert, AZ (US)

(73) Assignee: C.R. Bard, Inc., Franklin Lakes, NJ (US)

( * ) Notice: Subject to any disclaimer, the term of this patent is extended or adjusted under 35 U.S.C. 154(b) by 595 days.

This patent is subject to a terminal disclaimer.

(21) Appl. No.: 16/745,765

(22) Filed: Jan. 17, 2020

(65) Prior Publication Data
US 2020/0146710 A1 May 14, 2020

Related U.S. Application Data

(63) Continuation of application No. 15/210,603, filed on Jul. 14, 2016, now Pat. No. 10,561,438.
(Continued)

(51) Int. Cl.
*A61B 17/3207* (2006.01)
*A61B 17/22* (2006.01)
(Continued)

(52) U.S. Cl.
CPC ............... *A61B 17/320725* (2013.01); *A61B 17/22012* (2013.01); *A61M 25/09* (2013.01);
(Continued)

(58) Field of Classification Search
CPC ............ A61B 17/3207–320783; A61B 2017/320716–320791;
(Continued)

(56) References Cited

U.S. PATENT DOCUMENTS

| 5,624,449 A | 4/1997 | Pham et al. |
| 6,013,052 A * | 1/2000 | Durman ............ A61M 25/0144 604/95.01 |

(Continued)

FOREIGN PATENT DOCUMENTS

| CN | 201564947 U | 9/2010 |
| JP | H 05-137792 | 6/1993 |

(Continued)

*Primary Examiner* — Kelly J Bekker
*Assistant Examiner* — Mikail A Mannan
(74) *Attorney, Agent, or Firm* — Dickinson Wright PLLC; Andrew D. Dorisio

(57) ABSTRACT

A device for introduction into a body vessel includes a shaft, a balloon positioned at the distal end of the shaft, a guidewire disposed longitudinally within the shaft to receive a guidewire during use, a balloon disposed at the distal end of the shaft, and longitudinal scoring wires to score a vascular lesion attached to the distal end of the shaft, disposed over the balloon and disposed within the shaft. The proximal ends are welded or otherwise affixed to a spring mounted in the handle. The balloon expands when fluid is delivered to the balloon through the inflation lumen. This expansion pushes the scoring wires against the vascular lesion.

13 Claims, 9 Drawing Sheets

Related U.S. Application Data

(60) Provisional application No. 62/249,119, filed on Oct. 30, 2015.

(51) Int. Cl.
    *A61M 25/09* (2006.01)
    *A61M 25/10* (2013.01)
    *A61B 17/00* (2006.01)

(52) U.S. Cl.
    CPC . *A61M 25/104* (2013.01); *A61B 2017/00477* (2013.01); *A61B 2017/00778* (2013.01); *A61B 2017/22014* (2013.01); *A61B 2017/22061* (2013.01); *A61M 2025/1086* (2013.01); *A61M 2025/1093* (2013.01)

(58) Field of Classification Search
    CPC .............. A61B 17/32–320036; A61B 2017/320004–320056; A61B 17/320725; A61M 25/104; A61M 2025/1086; A61M 2025/1056; A61M 2025/1093; A61M 2025/109; A61M 25/10; A61M 2025/1004; A61M 2025/1031; A61M 2025/105
    See application file for complete search history.

(56) References Cited

U.S. PATENT DOCUMENTS

| | | | |
|---|---|---|---|
| 2003/0114877 A1* | 6/2003 | Gellman | A61M 25/10 606/192 |
| 2004/0034384 A1 | 2/2004 | Fukaya | |
| 2016/0113662 A1* | 4/2016 | Kobayashi | A61B 17/221 606/127 |

FOREIGN PATENT DOCUMENTS

| | | | |
|---|---|---|---|
| JP | 2004267323 A | | 9/2004 |
| JP | 2012196321 A | | 10/2012 |
| WO | 9117714 A1 | | 11/1991 |
| WO | 9531142 A1 | | 11/1995 |
| WO | WO9853616 | | 8/1998 |

\* cited by examiner

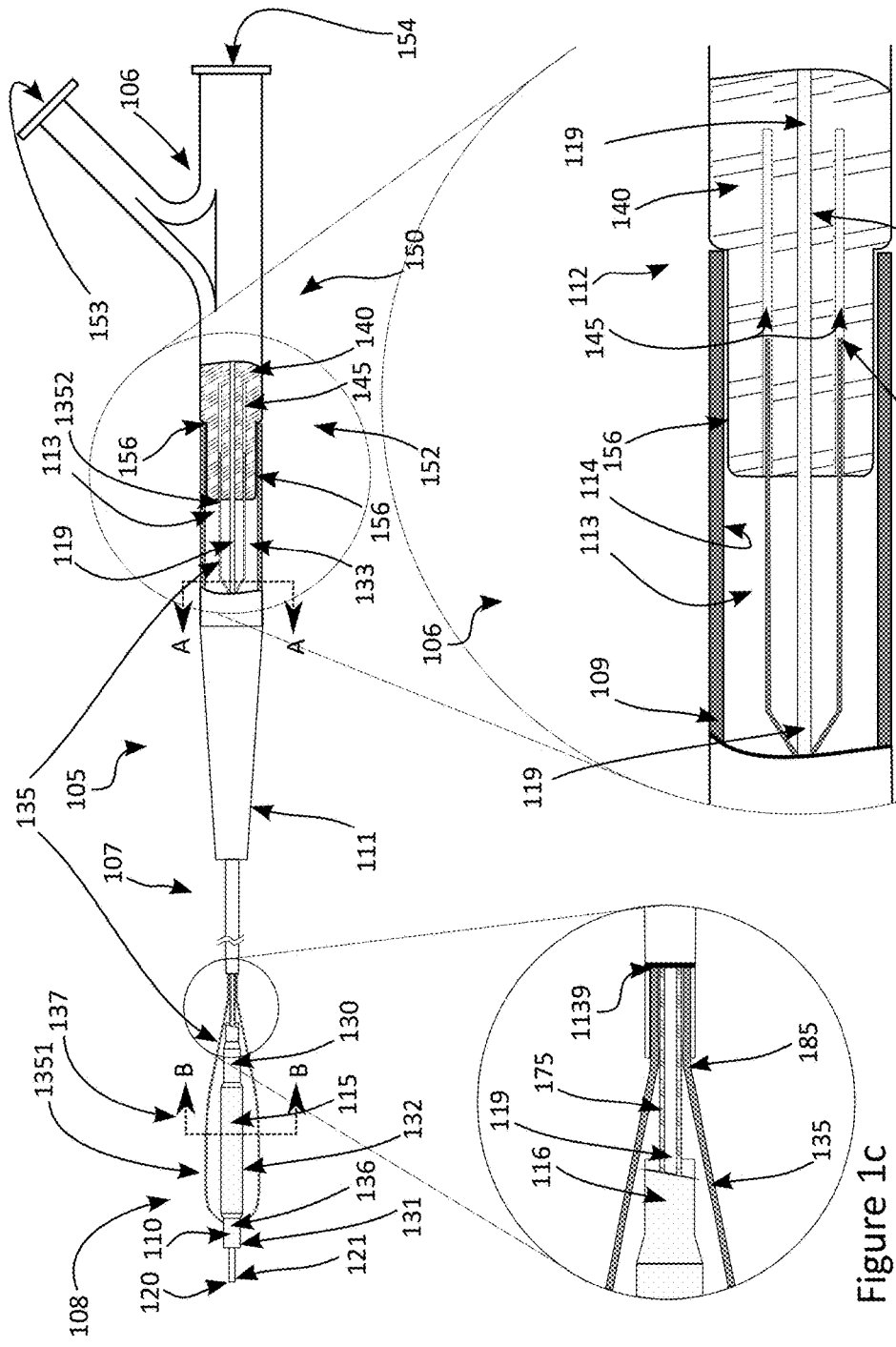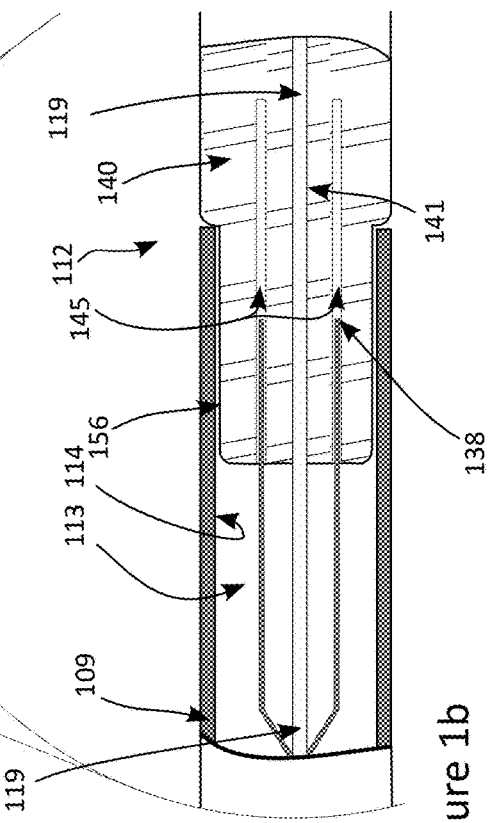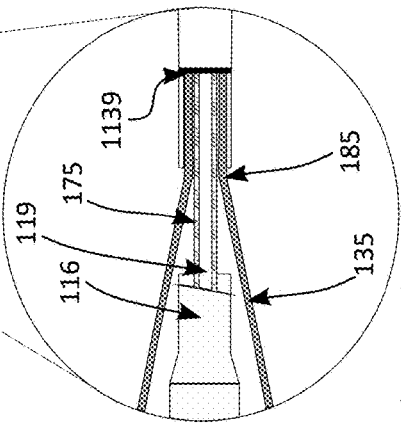
Figure 1a
Figure 1b
Figure 1c

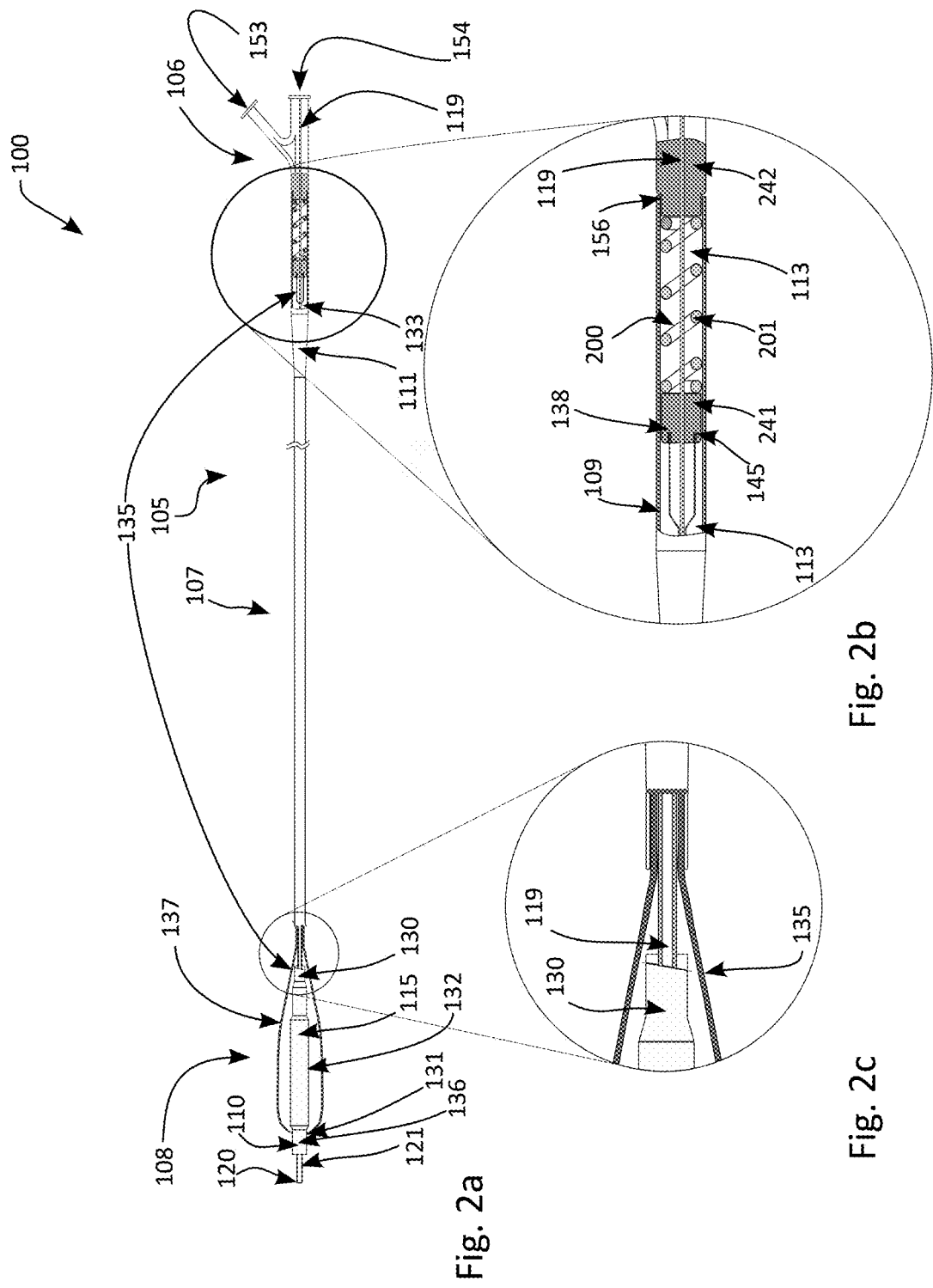

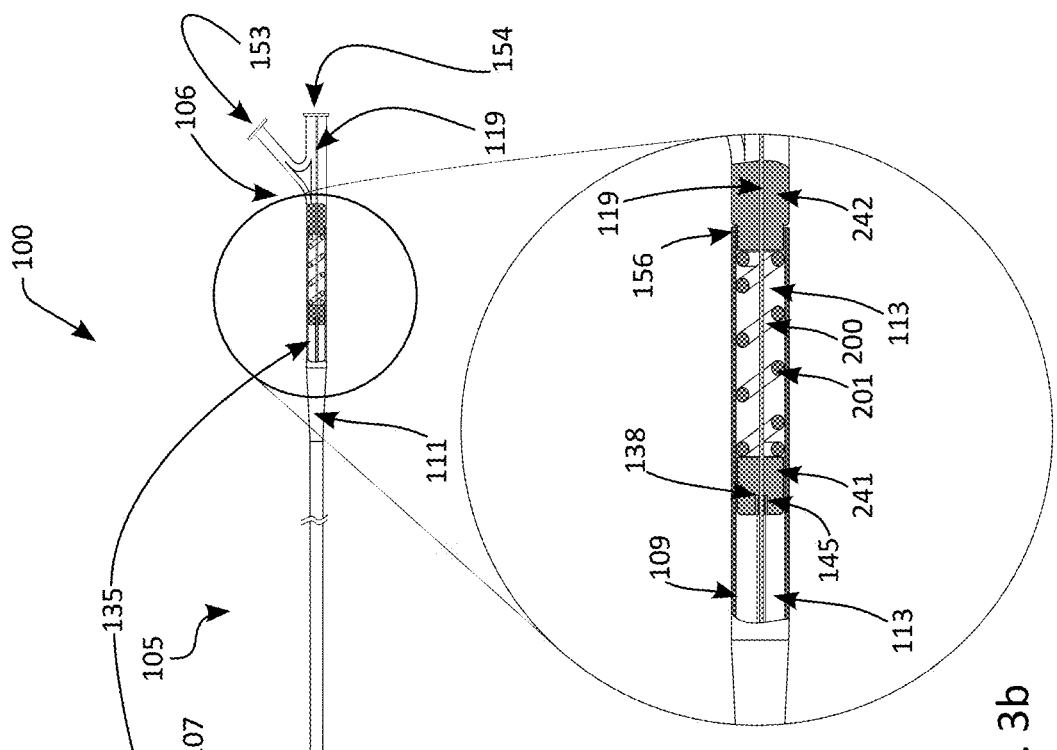
Fig. 3a
Fig. 3b
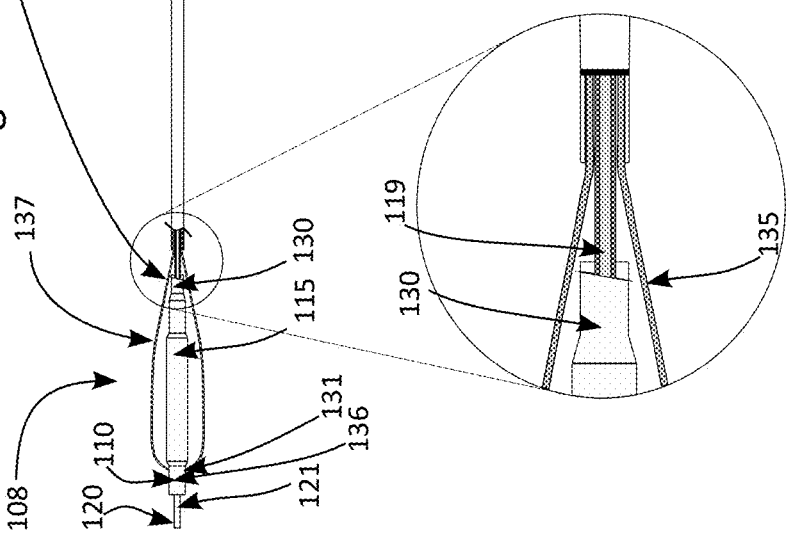
Fig. 3c

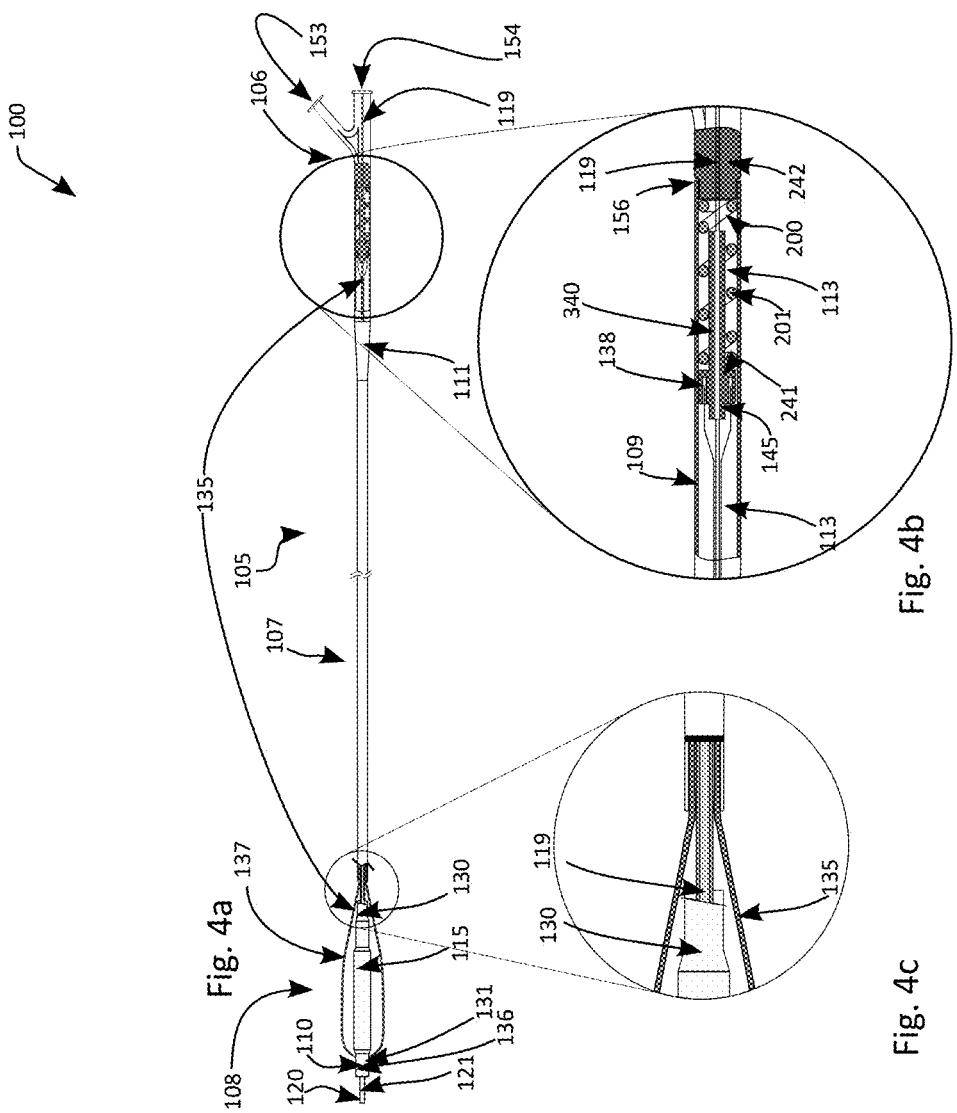

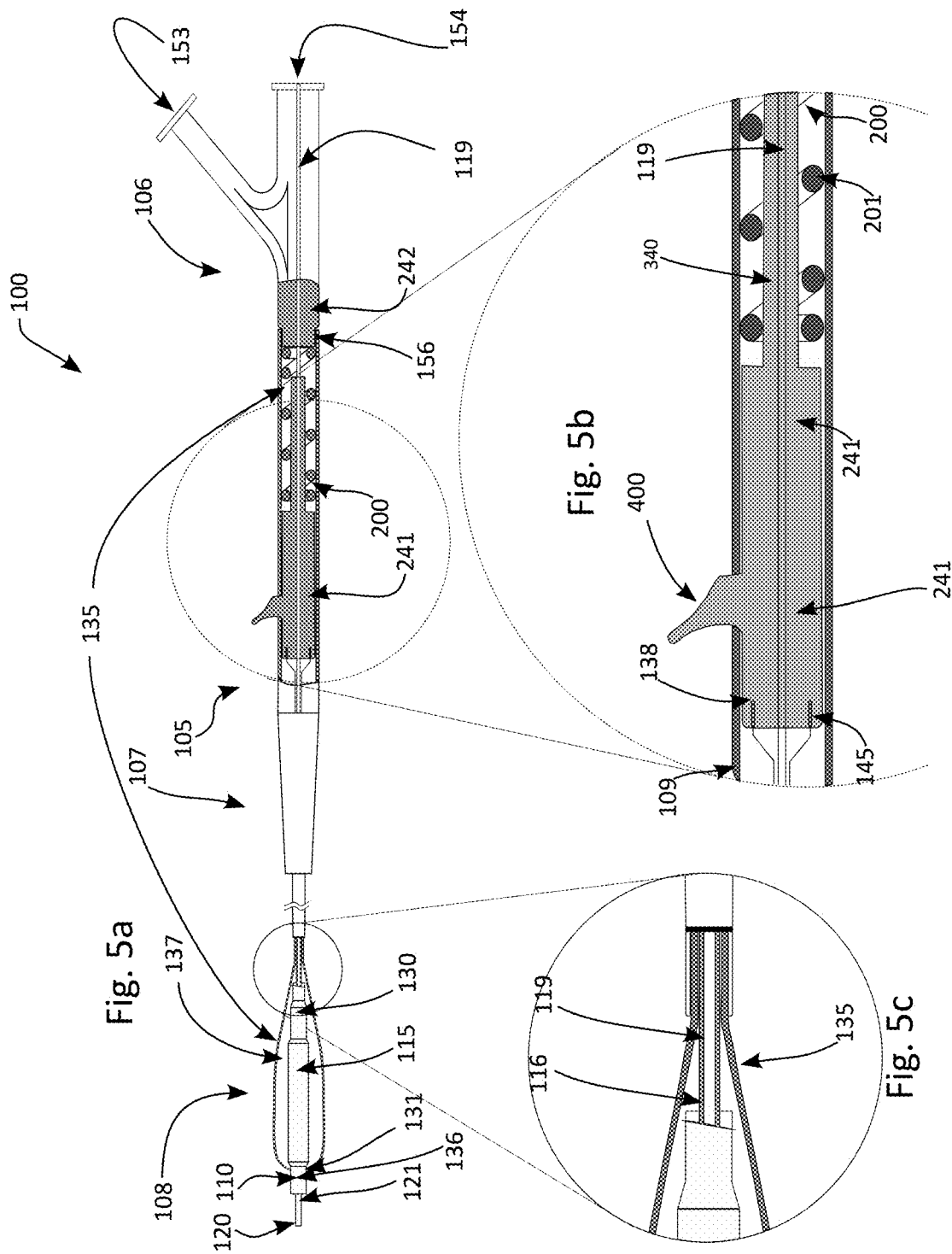

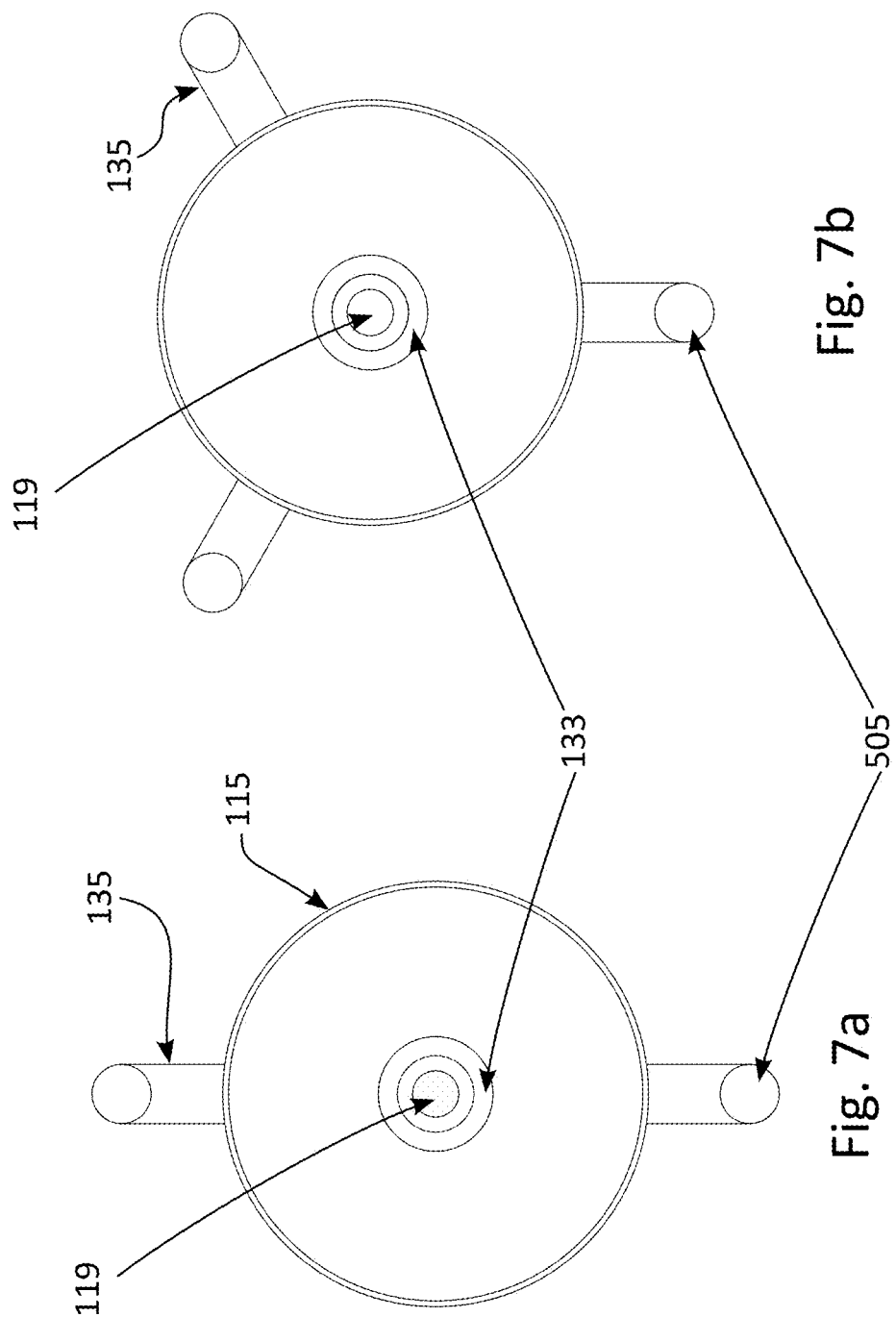

SCORING BALLOON WITH TRANSLATING SCORING WIRES

This application is a continuation of U.S. application Ser. No. 15/210,603 filed on Jul. 14, 2016 which claims priority to U.S. provisional App. No. 62/249,119 filed on Oct. 30, 2015, which are incorporated herein by reference.

BACKGROUND OF THE INVENTION

Balloon dilatation catheters are used to treat lesions in vessels. However, difficulties are encountered in navigating tortuous anatomy and safely crossing very tight lesions. Moreover, some lesions are difficult to dilate using just a balloon, and require a focused force to dilate the lesion at safe inflation pressures.

U.S. Pat. No. 6,394,995 to Solar et al. describes a system used to provide enhanced force to treat a lesion. This system has a flexible advancement member with a tracking member slidable over a guidewire, and a balloon having a distal end attached to the tracking member. But this type of system provides limited focused force and lacks pushability and maneuverability.

SUMMARY OF THE INVENTION

The present invention provides a scoring balloon catheter that can be used for treating vascular lesions. In use, the balloon presses scoring wires into the lesion. The catheter includes a shaft; an inflatable balloon mounted on the shaft's distal section; a member or spring associated with the shaft, proximal to the balloon; and at least one scoring wire. In some embodiments the scoring wire has a fixed end mounted on the shaft between the shaft's distal end and the balloon. The scoring wire has a longitudinally movable end associated with the member or spring; and an intermediate portion disposed outside of the balloon.

In some embodiments the movable scoring-wire ends are the proximal ends of the wires. These ends extend into lumens in the member. In some of these embodiments, the member comprises or interacts with a longitudinally resilient member such as an elastic polymer or rubber or a spring. In some embodiments, the device further comprises a second member in which the spring sits between the member and the second member.

In some embodiments, the device comprises scoring wire lumens inside or outside of the shaft. These scoring wire lumens contain one or more scoring wires. In some embodiments, the device comprises two lumens inside of the shaft and two scoring wires inside of the lumens.

In other embodiments, the scoring balloon catheter uses a spring mounted within a hub on a handle assembly. The shaft passes through the spring and extends into the handle assembly. A hub cover sits over the shaft and over the hub. In some cases, the hub cover provides strain relieve to the hub-spring connection. The scoring wires are welded or otherwise attached to the spring.

BRIEF DESCRIPTION OF THE DRAWINGS

The above and further advantages of the present invention may be better understood by referring to the following description in conjunction with the accompanying drawings in which:

FIG. 1a is a front view of an example of an invention device.

FIG. 1b is a magnified view of the indicated portion of FIG. 1a.

FIG. 1c is a magnified view of the indicated portion of FIG. 1a.

FIG. 2a is a front view of another example of an invention device.

FIG. 2b is a magnified view of the indicated portion of FIG. 2a.

FIG. 2c is a magnified view of the indicated portion of FIG. 2a.

FIG. 3a is a front view of another example of an invention device.

FIG. 3b is a magnified view of the indicated portion of FIG. 3a.

FIG. 3c is a magnified view of the indicated portion of FIG. 3a.

FIG. 4a is a front view of another example of an invention device.

FIG. 4b is a magnified view of the indicated portion of FIG. 4a.

FIG. 4c is a magnified view of the indicated portion of FIG. 4a.

FIG. 5a is a front view of another example of an invention device.

FIG. 5b is a magnified view of the indicated portion of FIG. 5a.

FIG. 5c is a magnified view of the indicated portion of FIG. 5a.

FIG. 7a is an end view showing the embodiment of FIG. 1 at section plane AA.

FIG. 7b is similar to FIG. 7a viewing section plane AA on a different invention embodiment.

Figure 6:
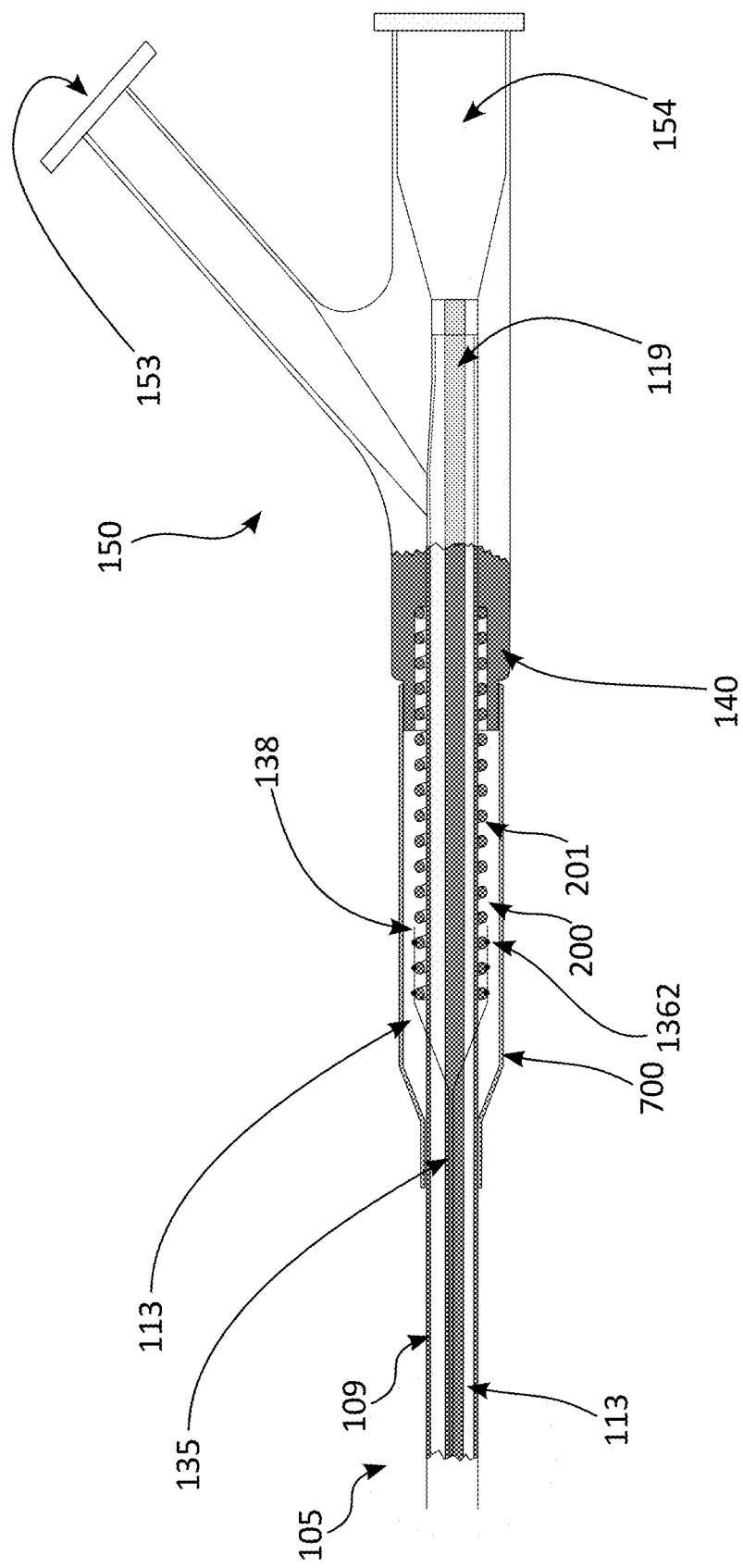
FIG. 6 is a front view of another embodiment of an invention device.

The drawings are not necessarily drawn proportionally or to scale. For example, the dimensions of some of the elements may be exaggerated relative to other elements for clarity or several physical components may be included in one functional block or element. Further, sometimes reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth to provide a thorough understanding of the present invention. Those of ordinary skill in the art will know that the present invention may be practiced without these specific details. In other instances, well-known methods, procedures, components, or structures may not have been described in detail so as not to obscure the present invention.

The present invention is directed to systems and methods for treatment of a vessel. The principles and operation of systems and methods of the present invention may be better understood with reference to the drawings and accompanying descriptions.

The invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

Certain features of the invention that are, for clarity, described in the context of separate embodiments, may also be provided in combination in a single embodiment. Conversely, various features of the invention that are, for brevity, described in the context of a single embodiment, may also be provided separately or in any suitable sub-combination.

Table of components.

| | |
|---|---|
| 100 | scoring balloon (SCB) catheter |
| 105 | shaft |
| 106 | shaft proximal section |
| 107 | shaft middle section |
| 108 | shaft distal section |
| 109 | shaft wall |
| 110 | shaft distal end |
| 111 | shaft tapered section |
| 112 | shaft proximal end |
| 113 | shaft lumen |
| 115 | inflatable balloon (IB) |
| 119 | guidewire lumen (GWL) |
| 120 | GWL distal end |
| 121 | GWL outer surface |
| 130 | IB proximal end |
| 131 | IB distal end |
| 132 | IB outer surface |
| 133 | IB lumen |
| 135 | scoring wire (SCW) |
| 1351 | SCW distal section |
| 1352 | SCW proximal section |
| 136 | fixed SCW end |
| 1361 | SCW lumen section |
| 1362 | weld joint |
| 137 | SCW IB section |
| 138 | moveable SCW end |
| 1139 | SCW lumen |
| 140 | Hub |
| 141 | GWL passage |
| 145 | Hub lumen |
| 150 | handle assembly (HA) |
| 153 | HA IB lumen port |
| 154 | HA GW port |
| 155 | HA distal end point |
| 156 | HA stepped-down portion |
| 200 | spring |
| 201 | spring wire |
| 241 | Hub distal section |
| 242 | hub proximal section |
| 340 | narrowed region |
| 400 | fingergrip |
| 451 | extension |
| 505 | SCW cross-section |
| 610 | see IBL |
| 700 | Hub cover |

Definitions

"fixed"—inseparable within the operational environment of the device.

"operational environment"—any environment in which the device would conceivably operate as an intravascular balloon catheter.

"longitudinally resilient"—the ability to repeatedly move longitudinally.

"definition of mechanically communicating"—describes the ability of one object to connect sufficiently such that its movement causes another object to move and vice versa.

"rail"—A substantially longitudinal object that supports and guides the movement of another object.

A "slidably engaged" component is a component that fits into a passageway or around a rail such that the component is largely or substantially constrained in two dimensions. Instead of the third dimension constraining the component, the component is unconstrained to some degree allowing the component to move longitudinally a substantial distance within the passageway or along the rail. If the system has stops or other components that curtail longitudinal movement, but still permit substantial longitudinal motion, the component is considered slidably engaged.

"effectively engaged"—a scoring wire is effectively engaged when it engages the lesion well enough for the treatment to substantially affect the lesion.

Invention catheters can be over-the-wire, short rapid exchange, or rapid exchange platform. If the catheter is a short rapid exchange platform, an inner member may traverse the entire length of the catheter.

Turning to the invention embodiments, FIG. 1a depicts an embodiment of the invention device. In this invention embodiment, a scoring balloon (SCB) catheter 100 is shown in a front view with selected sections shown in a magnified view. SCB catheter 100 comprises components as discussed below. For instance, catheter 100 comprises shaft 105. Shaft 105 has shaft proximal section 106 connected to shaft middle section 107 and shaft middle section 107 connected to shaft distal section 108. Shaft tapered section 111 joins shaft proximal section 106 to shaft middle section 107. Shaft 105 also comprises shaft wall 109, which provides a degree of rigidity to shaft 105 such that shaft 105 is suitable (as judged by those of ordinary skill in the art) for tracking into vasculature or tortuous vasculature being neither too rigid or too flexible. In some embodiments, the rigidity or flexibility is modified by adding a longitudinal member (not shown) to SCB catheter 100. Shaft 105 comprises Pebax, in some embodiments.

In some embodiments, shaft tapered section 111 is fixed to shaft middle section 107. In some embodiments, shaft wall 109 ends before shaft distal end 110 ends.

For purposes of this document, shaft distal end 110 is the end of shaft 105 that enters the patient first. Similarly, any other "distal"-characterized component means the component portion closer to shaft distal end 110 then is any other component portion. Likewise, any "proximal"-characterized component means the component portion further from shaft distal end 110 then is any other component portion.

SCB catheter 100 further comprises inflatable balloon (IB) 115. Inflatable balloon 115 mounts to shaft 105 within shaft distal section 108. In some embodiments, inflatable balloon 115 ends at shaft distal end 110. In these or other embodiments, inflatable balloon 115 is fixed to shaft 105.

Inflatable balloon 115 comprises IB proximal end 130 and IB distal end 131. A typical embodiment has a flexible, polymeric film serving as inflatable balloon 115. IB outer surface 132 ends up facing abluminally after inflatable balloon 115 mounts to shaft 105. For this disclosure, IB proximal end 130 is the portion of inflatable balloon 115 that attaches or fixes the proximal end of inflatable balloon 115 to shaft 105. IB proximal end 130 is defined as the proximal portion of inflatable balloon 115 that remains contacting shaft 105 after inflatable balloon 115 is inflated.

For this disclosure, IB distal end 131 is the portion of inflatable balloon 115 that distally attaches or fixes inflatable balloon 115 to shaft 105. IB distal end 131 is defined as the distal portion of inflatable balloon 115 that remains contacting shaft 105 after inflatable balloon 115 in inflated.

IB lumen 133 fluidly communicates with inflatable balloon 115, which allows inflatable balloon 115 to be inflated by fluid passing through IB lumen 133.

SCB catheter 100 further comprises guidewire lumen (GWL) 119, which longitudinally extends at least from shaft proximal end 112 to beyond shaft distal end 110. GW lumen 119 ends at GWL distal end 120.

In some embodiments, IB proximal end 130 and IB distal end 131 connect to GWL outer surface 121 or shaft 105 using any method known to those of ordinary skill in the art.

SCB catheter 100 further comprises scoring wire (SCW) 135. Scoring wire 135 comprises fixed SCW end 136, SCW IB section 137, and movable SCW end 138. Fixed SCW end 136 connects within shaft distal section 108 distal of IB distal end 131. In some embodiments, fixed SCW end 136 attaches to GWL outer surface 121. In other embodiments, fixed SCW end 136 attaches to the outer side of shaft wall 109. Fixed SCW end 136 attaches using any method known to those of ordinary skill in the art.

This configuration provides for a focused force element (scoring wire 135) alongside inflatable balloon 115.

The distance between scoring wire 135 and IB outer surface 132 can be any value recognized as useful by those of ordinary skill in the art. Once past inflatable balloon 115, scoring wire 135 dives below shaft wall 109, extending proximally inside of shaft 105. Movable SCW end 138 sits inside of shaft 105 within shaft proximal section 106. In some embodiments, scoring wire 135 occupies at least part of SCW lumen 1139 (shown in FIGS. 8a and 8b).

FIG. 1a-FIG. 5b depicts SCB catheter 100 as having two scoring wires. In some embodiments, SCB catheter 100 has 1-15, 3-10, or 2-5 scoring wires. In some embodiments the diameter of SCW 135 is between 0.003 inches and 0.040 inches, or 0.005 inches and 0.015 inches, 0.008 inches and 0.012 inches. In some embodiments, SCW 135 is 0.10 inches. SCW 135 need not have a uniform diameter. In some embodiments SCW distal section 1351 has a diameter larger than SCW proximal section 1352. In some embodiments SCW distal section 1351 has a diameter smaller than SCW proximal section 1352. In some embodiments, SCW 135 comprises metals, metal alloys, polymers, and shape memory materials that are metal- or polymer-based.

SCB catheter 100 further comprises hub 140. Hub 140 resides inside of shaft 105 within shaft proximal section 106. Hub 140 comprises a GWL passage 141 for guidewire lumen 119 to pass through. Hub 140 further comprises one or more hub lumens 145 that interact with movable SCW end 138.

In some embodiments, the interaction encompasses movable SCW end 138 connected in or to hub lumen 145. In some embodiments, movable SCW end 138 is fixed to hub lumen 145. In other embodiments, the interaction encompasses movable SCW end 138 being slidably engaged inside of hub lumen 145. In some embodiments hub 140 comprises any biocompatible material such as metals, metal alloys, and polymers. In some embodiments hub 140 comprises nylon, Pebax, or any other suitable material known to those of ordinary skill in the art.

In some embodiments hub 140 is substantially fixed inside shaft proximal section 106 with movable SCW end 138 slidably engaged or disposed within hub lumen 145. In some embodiments, hub 140 is longitudinally movable or elastic, allowing movable SCW end 138 to move longitudinally by pulling hub 140 distally, by moving hub 140 or by stretching material of hub 140. For instance, in some embodiments, hub 140 is elastic. When movable SCW end 138 is subjected to a distally directed force that causes it to move distally and when movable SCW end 138 is fixed to or within hub lumen 145, the movement stretches hub 140. The restoring force or force counter to that distal stretching (counterforce) tends to move movable SCW end 138 substantially back into place when the distally directed force is removed.

In some embodiments, hub 140 is biased by a spring 200. In some embodiments, spring 200 mounts distal to hub 140 and in some embodiments, spring 200 mounts proximal to hub 140.

SCW catheter 100 further comprises handle assembly 150. Handle assembly 150 associates with shaft proximal end 109. Handle assembly 150 comprises HA port sub-assembly and HA transition sub-assembly. HA port sub-assembly occupies at least part of the proximal end of handle assembly 150. And HA transition sub-assembly occupies at least part of the distal end of handle assembly 150. HA port sub-assembly relates to HA transition sub-assembly. In some embodiments, HA port sub-assembly connects to or is fixed to HA transition sub-assembly. In some embodiments, HA port sub-assembly and HA transition sub-assembly together form a monolithic object or a number of objects or monolithic objects split by a plane containing SCW catheter 100's longitudinal axis.

HA transition sub-assembly comprises HA stepped-down portion 156 located at the distal end of HA transition sub-assembly. In some embodiments the distal end of HA transition sub-assembly and the distal end of handle assembly 150 are the same object.

HA stepped-down portion 156 is a portion of HA transition sub-assembly in which the overall outside dimension has a step transition decreasing to a smaller diameter, sized to engage shaft proximal end 112.

In some embodiments, transition subassembly 152 does not have HA stepped-down portion 156.

Shaft 105 relates to handle assembly 150 through shaft proximal end 112 and HA stepped-down portion 156. In some embodiments, shaft 105 connects to handle assembly 150. For example, shaft proximal end 112 can slide over HA stepped-down portion 156 and the components can be fixed such as by welding, fusing, gluing, etc. Or the friction fit between shaft proximal end 112 and HA transition sub-assembly can be strong enough to fix the components together. In some embodiments lacking HA stepped-down portion 156, shaft proximal end 112 can connect to handle assembly 150 through a butt joint between shaft proximal end 112 and HA transition subassembly 152.

HA port sub-assembly comprises HA GW port 154, which occupies the proximal end of HA port sub-assembly. In some versions of handle assembly 150, HA GW port 154 points away or directly away from shaft distal end 110. HA GW port 154 allows access from outside of SCB catheter 100 into guidewire lumen 119. In some versions of handle assembly 150, HA port subassembly also comprises HA IB lumen port 153, which angles out from the longitudinal axis of SCB catheter 100 at any of a variety of angles recognized as useful to those of ordinary skill in the art. In some versions, HA IB lumen port 153 flows into the guidewire-port-guidewire-lumen region and in other embodiments flows to a separate lumen inside or outside (not shown) of guidewire lumen 119. HA IB lumen port 153 also allows access from outside of SCB catheter 100 into a passageway (guidewire lumen 119 or IB lumen 133 (IBL)) that carries gas or inflation fluid into inflatable balloon 115 to inflate it or carries gas or inflation fluid out of inflatable balloon 115 to deflate it.

Operationally, in the devices taught by the FIG. 1a embodiment, for treatment of calcified lesions, for example, a physician cuts through the patient's tissue until an appropriately sized vessel is revealed. The vessel must lead to the lesion site following a path that SCB catheter 100 can follow. In some embodiments, the location of the lesion site causes those of ordinary skill in the art to select a more or less flexible shaft 105 or SCB catheter 100.

The physician opens the vessel, inserts a guidewire into the vessel, and advances the guidewire through the patient's vasculature under ultrasound, magnetic resonance, fluoroscopic, or some other type of guidance. Once the physician places the guidewire at a satisfactory site, the physician threads the proximal end of the guidewire into GWL distal end 120, through guidewire lumen 119, and ultimately out of SCB catheter 100—through HA GW port 154. With the guidewire in place and installed in SCB catheter 100, the physician maneuvers SCB catheter 100 along the guidewire until inflatable balloon 115 reaches the desired position near the lesion site. Typically, this position will allow at least one scoring wire 135 to effectively engage the lesion. After that, the physician inflates inflatable balloon 115 until scoring wire 135 firmly presses into or cracks the lesion. Once lesion treatment with SCB catheter 100 is complete, the physician deflates inflatable balloon 115, which allows scoring wire 135 to relax away from the lesion and from the vessel wall.

Scoring wire 135 contacts the lesion as long as inflatable balloon 115 remains inflated. The inflation time corresponds to the time the physician chooses for scoring wire 135 to contact the lesion. Those of ordinary skill in the art use inflation times of 5 seconds to 5 minutes. Those of ordinary skill in the art look to the nature of the lesion in determining the appropriate inflation time and inflation speed.

An aspect of this invention includes the behavior of scoring wire 135 during balloon inflation and specifically includes the behavior of movable SCW end 138.

As inflatable balloon 115 inflates, scoring wire (or wires) 135 expands outwardly, placing scoring wire 135 under longitudinal tension. A component of the force vector caused by that longitudinal tension points proximally from fixed SCW end 136 and distally from movable SCW end 138. But fixed SCW end 136 is fixed to shaft 105 or GWL outer surface 121. Therefore, any movement of scoring wire 135 occurs at movable SCW end 138. Hub 140 constrains the movement of movable SCW end 138 allowing it to move longitudinally. This movement decreases the strain on inflatable balloon 115 helping to maintain its engineered shape and helping to avoid any kinking in the balloon's net, which was sometimes seen in prior art devices having scoring wires substantially fixed at both ends.

When the physician deflates the balloon, the forces previously causing scoring wire 135 to expand disappear, allowing scoring wire 135 (and movable SCW end 138) to relax. Hub 140 constrains the relaxation of movable SCW end 138. Specifically, hub 140 guides movable SCW end 138 into an arrangement similar to the initial arrangement of movable SCW end 138 before balloon inflation. Hub 140's action helps regularize the inflation and deflation steps increasing their predictability.

Returning to FIG. 1a, FIG. 1a depicts the catheter as described above. The specific shaft 105 can be made by a variety of methods as known to those of ordinary skill in the art. The embodiment shown in FIG. 1a comprises shaft 105 coupled (attached, connected, joined) to handle assembly 150 through HA distal end portion 155 and HA stepped-down portion 156. HA stepped-down portion 156 occupies shaft lumen 113 and substantially seals shaft proximal end 112 from the atmosphere. In some embodiments, shaft proximal end 112 and HA distal end portion 155 are glued together with an adhesive. In other embodiments, an adhesive is not used. Those of ordinary skill in the art know of other joining methods. These are considered to be within the scope of the current invention.

In FIG. 1a, HA stepped-down portion 156 sits midway along HA distal end portion 155's length. Moreover, in this embodiment HA distal end portion 155 also serves as hub 140. The reference numbers refer to the same component because the component serves both as HA distal end 155 and as hub 140.

FIG. 1b is magnified view of shaft proximal section 106. Shaft 105 ends at shaft proximal end 112 and receives hub 140, which is either part of HA distal end 155 or not. Hub 140 can have one or more hub lumens 145—FIG. 1b shows two hub lumens 145. These hub lumens 145 extend into hub 140 longitudinally in this embodiment. But SCB catheter 100 does not need lengthwise hub lumens 145 to function correctly. Hub lumens 145 need only function to slidably and reversibly receive movable SCW end 138. FIG. 1b shows hub lumens 145 extending into hub 140 approximately three quarters of hub 140's length, but this is not critical. In some embodiments, hub lumens 145 extend completely through hub 140. Hub lumens 145 extend into hub 140 as far as or further than movable SCW end 138 extends into hub lumen 145. FIG. 1b also shows scoring wire 135 and movable SCW end 138. In this embodiment, scoring wire 135 tapers or flares outwardly after proximally exiting SCW lumen 1139. Movable SCW end 138 occupies a portion of hub lumen 145. In this embodiment, SCB catheter 100 comprises one hub lumen 145 per movable SCW end 138. But other embodiments exist in which a hub lumen can interact with more than one movable SCW end 138.

Finally, FIG. 1b shows guidewire lumen 119 passing through hub 140 and continuing into shaft 105. FIG. 1c depicts a magnified view of the region where scoring wire 135 distally exits SCW lumen 1139.

Scoring wire 135 has a path through part of SCB catheter 100. SCW lumen 1139 is a lumen that receives scoring wire 135 along some or all of shaft middle section 107. We refer to the portion of scoring wire 135 within SCW lumen 1139 as SCW lumen section 1361. And we refer to the section of scoring wire 135 near inflatable balloon 115 as SCW IB section 137.

For discussion purposes, we begin the path at movable SCW end 138. Movable SCW end 138 resides within hub lumen 145. As we move distally along scoring wire 135, we come to the proximal end of SCW lumen 1139, which scoring wire 135 occupies. In some embodiments, scoring wire 135 tapers inwardly proximally of SCW lumen 1139. Scoring wire 135 distally exits SCW lumen 1139 at the lumen's distal end. We refer to the section of scoring wire 135 that begins at this exit as SCW IB section 137. After exiting, scoring wire 135 flares outward as it progresses distally, extending in a substantially longitudinal direction until the wire is past IB distal end 131. At that point scoring wire 135 turns inwardly until it reaches shaft distal section 108 or GWL outer surface 121. Fixed SCW end 136 attaches to SCB catheter 100 distally of inflatable balloon 115 or at or near the point where IB distal end 131 attaches to SCB catheter 100. The portion of scoring wire 135 within SCW IB section 137 has a longitudinal region along inflatable balloon 115. The distance this longitudinal section extends from SCB catheter 100's central axis (wire distance) can have a variety of values. The distance that IB outer surface 132 extends from the central axis when inflatable balloon 115 inflates is the balloon inflation distance. Typically, (wired distance)/(balloon inflation distance) is within the following ranges 0.99-1.01; 0.90-1.1; 0.8-1.2; and 0.5-1.5.

In the operation of the group of embodiments represented by the device in FIG. 1a, a physician places inflatable balloon 115 as described above. The physician inflates inflatable balloon 115 through HA IB lumen port 153. Balloon inflation first applies outward pressure on scoring wires 135 and then onto the lesion. Without wishing to be bound by any particular theory of operation, we believe that because movable SCW end 138 is moveably connected, scoring wire 135 does not contribute to balloon or balloon deformation caused by inflation or overinflation. Since the wire can move outwardly, it does not significantly cage the balloon. The caging effect will prevent the balloon from expanding past the wires. But if inflation continues, some other portion of the balloon will deform from the pressure exerted by the inflation fluid. In some cases balloon deformation leads to problems with later deflating the balloon. Instead, the outwardly directed inflation pressure on scoring wire 135 causes movable SCW end 138 to move distally, which lowers the counterforce that scoring wire 135 exerts against inflatable balloon 115. As movable SCW end 138 moves distally, it recedes from hub lumen 145. In some embodiments, inflation pressure causes movable SCW end 138 to pull out of hub lumen 145. In other embodiments, movable SCW end 138 remains inside of hub lumen 145.

The physician maintains pressure in inflatable balloon 115 long enough for scoring wire 135 to have the effect the physician desires. Afterward, the physician releases pressure, inflatable balloon 115 deflates, and movable SCW end 138 re-extends into hub lumen 145.

FIGS. 2a through 2c depict different embodiments of SCB catheter 100. These embodiments are similar to those shown in FIGS. 1a through 1c. The main difference between the sets of embodiments lies in the hub and the proximal scoring wire geometry.

FIG. 2b depicts a hub 140 that has hub distal section 241 and hub proximal section 242. Hub proximal section 242 through HA stepped-down portion 156 serves to connect shaft 105 with handle assembly 150. Additionally, hub proximal section 242 serves as a stop for spring 200. Spring 200 comprises spring wire 201—the figure depicts spring wire 201 in cross-section. Spring 200 adds resilience to the mechanism of scoring wire 135.

Hub distal section 241 lies next to the distal end of spring 200. Hub distal section 241 connects (attaches) to movable SCW end 138. In some embodiments, hub distal section 241 is fixed to movable SCW end 138. In other embodiments, hub distal section 241 comprises hub lumens 145, which in some cases are fixed to movable SCW end 138. Movable SCW end 138 flares outwardly as it reaches hub distal section 241. In this embodiment, on the other hand, the embodiment shown in FIG. 3a through 3c comprise movable SCW ends 138 that do not flare as it reaches hub distal section 241.

In the operation of the group of embodiments represented by the devices disclosed in FIGS. 1a-6, a physician places inflatable balloon 115 as described above. The physician inflates inflatable balloon 115 through HA IB lumen port 153, which first applies outer pressure on scoring wires 135 and then on the lesion. The difference in operation between the above embodiments and the group of embodiments represented by FIGS. 1a-3c is in the mechanism that that allows movement by movable SCW end 138. As in the above embodiments, in these embodiments, as inflatable balloon 115 inflates, the counterforce that scoring wire 135 would otherwise apply, is moderated by movable SCW end 138. In this group, movable SCW end 138 recedes distally as before, but hub distal section 241 also moves distally. The arrangement of hub distal section 241, spring 200, and hub proximal section 242 imparts force, through hub distal section 241, to movable SCW end 138. This force tends to proximally bias movable SCW end 138. And when the physician deflates the balloon as before, movable SCW end 138 moves proximally, substantially back to its initial position, aided by the force of spring 200.

FIGS. 4a-4b depict another embodiment of SCB catheter 100. The device of this embodiment is substantially similar to the embodiments described above. The main difference is that this version of hub distal section 241, although similar to hub distal sections described above, has narrowed region 340 that extends proximally from hub distal section 241. Narrowed region 340 sits inside of spring 200.

Similarly, FIG. 5a has narrowed region 340 and additionally has extension 451 sitting between hub distal section 241 and narrowed region 340. Finger grip 400 sits on extension 451, extending through the side of shaft proximal section 106. Finger grip 400 provides the physician some control of distal hub 450, which enables more direct control of movable SCW end 138 in these types of embodiments.

FIG. 6 discloses an embodiment of the proximal section of the device. In this embodiment a spring 200 sits within the distal end of HA 150 and extends distally from HA 150. Hub 140 connects to HA 150 and forms a monolithic structure with HA 150. Spring 200 receives shaft proximal section 106. Movable SCW end 138 exits scoring wire lumen 1139 near the distal end of shaft proximal section 106. Movable SCW end 138 connects directly to spring 200 through any suitable method, such as soldering, welding, overmolding, gluing, or press fitting using plastic tubing. In some embodiments, movable SCW end 138 connects directly to spring 200 through a weld joint 1362. In this or other embodiments, hub cover 700 sits over hub 140 and shaft 105. In some cases, hub cover 700 provides strain relieve for the connection between HA 150 and shaft 105.

The spring 200 provides longitudinal movement and a biasing force to movable SCW end 138. When movable SCW end 138 experiences a distally directed force that moves it distally, the movement holds that away from HA 150. The restoring force or force counter to that distal stretching (counterforce) tends to move movable SCW end 138 substantially back into place once the distally directed force disappears.

FIG. 7a depicts section AA of FIG. 1a. It shows two scoring wires 135, inflatable balloon 115, IB lumen 133, and guidewire lumen 119. As can be seen, section plane AA cuts through SCB catheter 100 at shaft distal section 108. The plane also cuts inflatable balloon 115; cuts scoring wire 135 at SCW IB section 137 showing SCW cross-section 505; and cuts guidewire lumen 119. FIG. 7b depicts a similar embodiment, but with three scoring wires 135.

Figure 8B:
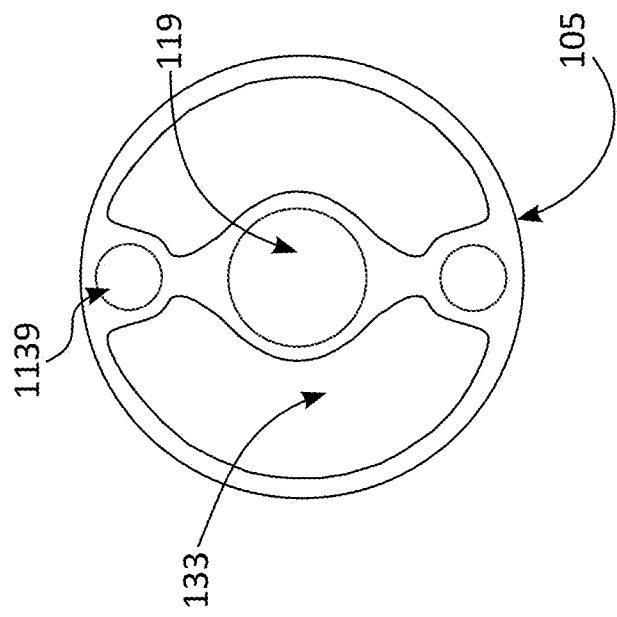
FIG. 8b is similar to FIG. 8a viewing section plane AA on a different invention embodiment.
Figure 8A:
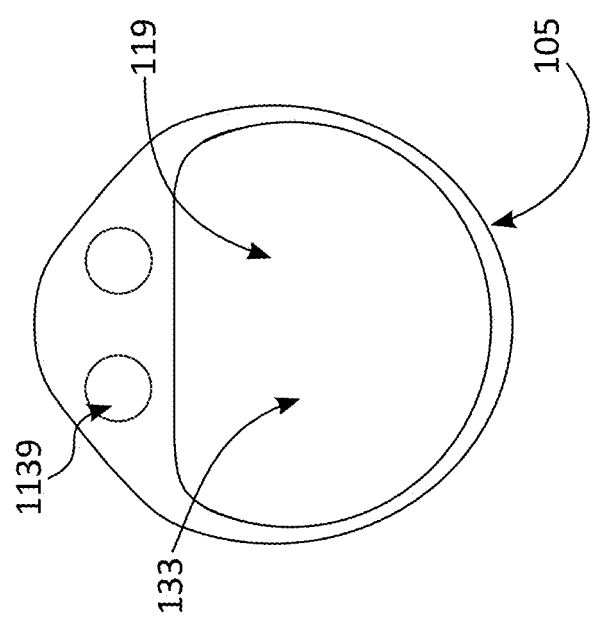
FIG. 8a is an end view showing an embodiment of the device taken along a section plane similar to section plane BB.

FIG. 8a depicts section BB of FIG. 1a. It shows two SCW lumens 1139 sitting side-by-side. It also shows IB lumen 133 and GW lumen 119. SCW lumen 1139 need not adopt a side-by-side configuration, as shown in this figure, but can adopt a configuration distributed around the perimeter of shaft 105.

FIG. 8b shows a different embodiment similar to FIG. 1a in cross-section. Shaft proximal section 106 is cut proximally of shaft tapered section 111. Shaft tapered section 111 tapers from shaft proximal section 106 to shaft middle section 107. Shaft 105 has shaft wall 109. For example, FIG.

8b depicts two SCW lumens 1139 distributed across from each other in shaft 105. This distribution need not be symmetric. Also in this figure, guidewire lumen 119 lies within shaft 105, and it shows SCW lumen 1139 extending longitudinally inside of shaft 105. In some embodiments, SCW lumens sit outside of the guidewire lumen.

Figure 9:
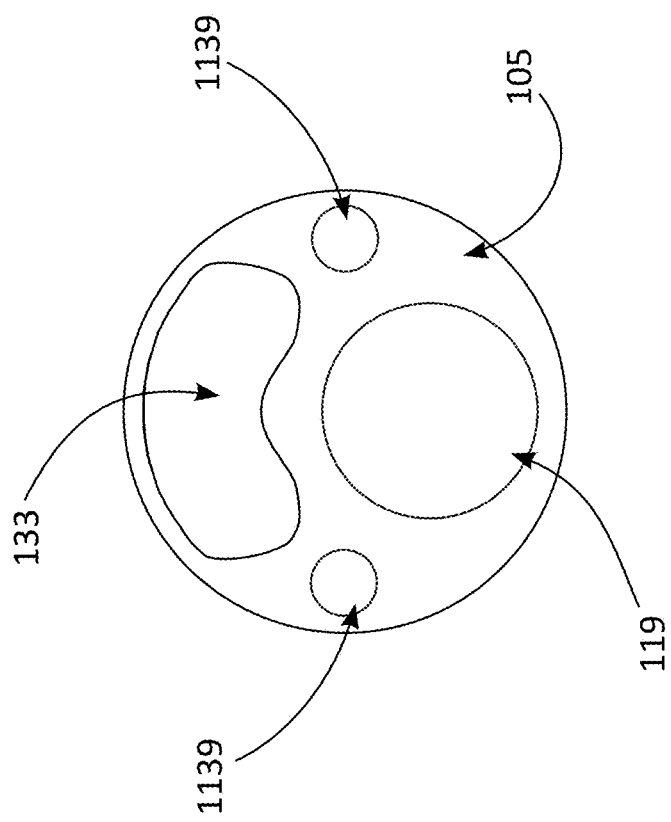
FIG. 9 is an end view of the device of FIG. 6.

FIG. 9 shows the embodiment of FIG. 6 in cross-section. In this figure, guidewire lumen 119 lies within shaft 105. In some embodiments, shaft 105 is an extrusion providing guidewire lumen 119, two SCW lumen 1139, and one lumen 133.

In any of the embodiments set out above, inflatable balloon 115 can have any of a variety of diameters ranging from 1.25-40 mm or 2.0-8.0 mm. In any of the embodiments set out above, inflatable balloon 115 can have any of a variety of lengths such as 10-300 mm or 20-300 mm. Long balloons may be particularly useful for treating peripheral lesions, which often have long diseased portions.

In all of the systems described above, a coating such as a hydrophobic or hydrophilic coating may be added externally to provide ease of insertion.

Suitable drugs or therapeutic agents include the following substances.

Antimicrobial agents may be selected, for example, from triclosan from triclosan, chlorhexidine, nitrofurazone, benzalkonium chlorides, silver salts and antibiotics such as rifampin, gentamycin and minocyclin and combinations thereof, among others.

In certain embodiments, antimicrobial agents may include triclosan, chlorhexidine and salts or combinations thereof. Anti-inflammatory agents include steroidal and non-steroidal anti-inflammatory agents. Examples of nonsteroidal anti-inflammatory drugs include aminoarylcarboxylic acid derivatives such as enfenamic acid, etofenamate, flufenamic acid, isonixin, meclofenamic acid, mefanamic acid, niflumic acid, talniflumate, terofenamate and tolfenamic acid; arylacetic acid derivatives such as acemetacin, alclofenac, amfenac, bufexamac, cinmetacin, clopirac, diclofenac sodium, etodolac, felbinac, fenclofenac, fenclorac, fenclozic acid, fentiazac, glucametacin, ibufenac, indomethacin, isofezolac, isoxepac, lonazolac, metiazinic acid, oxametacine, proglumetacin, sulindac, tiaramide, tolmetin and zomepirac; arylbutyric acid derivatives such as bumadizon, butibufen, fenbufen and xenbucin; arylcarboxylic acids such as clidanac, ketorolac and tinoridine; arylpropionic acid derivatives such as alminoprofen, benoxaprofen, bucloxic acid, carprofen, fenoprofen, flunoxaprofen, flurbiprofen, ibuprofen, ibuproxam, indoprofen, ketoprofen, loxoprofen, miroprofen, naproxen, oxaprozin, piketoprofen, pirprofen, pranoprofen, protizinic acid, suprofen and tiaprofenic acid; pyrazoles such as difenamizole and epirizole; pyrazolones such as apazone, benzpiperylon, feprazone, mofebutazone, morazone, oxyphenbutazone, phenybutazone, pipebuzone, propyphenazone, ramifenazone, suxibuzone and thiazolinobutazone; salicylic acid and its derivatives such as acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamine a-acetic acid, salicylsulfuric acid, salsalate and sulfasalazine; thiazinecarboxamides such as droxicam, isoxicam, piroxicam and tenoxicam; others such as Eacetamidocaproic acid, s-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole and tenidap; and pharmaceutically acceptable salts thereof.

Examples of steroidal anti-inflammatory agents (glucocorticoids) include 21-acetoxyprefnenolone, alclometasone, algestone, amicinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumehtasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol priopionate, halometasone, halopredone acetate, hydrocortamate, hydrocortisone, loteprednol etabonate, mazipredone, medrysone, meprednisone, methyolprednisolone, mometasone furoate, paramethasone, prednicarbate, prednisolone, prednisolone 25-diethylaminoacetate, prednisone sodium phosphate, prednisone, prednival, prednylidene, rimexolone, tixocortal, triamcinolone, triamcinolone acetonide, triamcinolone benetonide, triamcinolone hexacetonide, and pharmaceutically acceptable salts thereof.

Analgesic agents include narcotic and non-narcotic analgesics. Narcotic analgesic agents include alfentanil, allylprodine, alphaprodine, anileridine, benzylmorphine, bezitramide, buprenorphine, butorphanol, clonitazene, codeine, codeine methyl bromide, codeine phosphate, codeine sulfate, desomorphine, dextromoramide, dezocine, diampromide, dihydrocodeine, dihydrocodeinone enol acetate, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, hydrocodone, hydromorphone, hydroxypethidine, isomethadone, ketobemidone, levorphanol, lofentanil, meperidine, meptazinol, metazocine, methadone hydrochloride, metopon, morphine, myrophine, nalbuphine, narceine, nicomorphine, norlevorphanol, normethadone, normorphine, norpipanone, opium, oxycodone, oxymorphone, papaveretum, pentazocine, phenadoxone, phenazocine, pheoperidine, piminodine, piritramide, proheptazine, promedol, properidine, propiram, propoxyphene, rumifentanil, sufentanil, tilidine, and pharmaceutically acceptable salts thereof. Non-narcotic analgesics include aceclofenac, acetaminophen, acetaminosalol, acetanilide, acetylsalicylsalicylic acid, alclofenac, alminoprofen, aloxiprin, aluminum bis(acetylsalicylate), aminochlorthenoxazin, 2-amino-4-picoline, aminopropylon, aminopyrine, ammonium salicylate, amtolmetin guacil, antipyrine, antipyrine salicylate, antrafenine, apazone, aspirin, benorylate, benoxaprofen, benzpiperylon, benzydamine, bermoprofen, brofenac, p-bromoacetanilide, 5-bromosalicylic acid acetate, bucetin, bufexamac, bumadizon, butacetin, calcium acetylsalicylate, carbamazepine, carbiphene, carsalam, chloralantipyrine, chlorthenoxazin(e), choline salicylate, cinchophen, ciramadol, clometacin, cropropamide, crotethamide, dexoxadrol, difenamizole, diflunisal, dihydroxyaluminum acetylsalicylate, dipyrocetyl, dipyrone, emorfazone, enfenamic acid, epirizole, etersalate, ethenzamide, ethoxazene, etodolac, felbinac, fenoprofen, floctafenine, flufenamic acid, fluoresone, flupirtine, fluproquazone, flurbiprofen, fosfosal, gentisic acid, glafenine, ibufenac, imidazole salicylate, indomethacin, indoprofen, isofezolac, isoladol, isonixin, ketoprofen, ketorolac, plactophenetide, lefetamine, loxoprofen, lysine acetylsalicylate, magnesium acetylsalicylate, methotrimeprazine, metofoline, miroprofen, morazone, morpholine salicylate, naproxen, nefopam, nifenazone, 5' nitro-2' propoxyacetanilide, parsalmide, perisoxal, phenacetin, phenazopyridine hydrochloride, phenocoll, phenopyrazone, phenyl acetylsalicylate, phenyl salicylate, phenyramidol, pipebuzone, piperylone, prodilidine, propacetamol, propyphenazone, proxazole, quinine salicylate, ramifenazone, rimazolium metilsulfate, salacetamide, salicin, salicylamide, salicylamide a-acetic acid, salicylsulfuric acid, salsalte, salverine, simetride, sodium salicylate, sulfamipyrine, suprofen, talniflumate, tenoxicam, terofenamate, tetradrine, tinoridine, tolfenamic acid, tolpronine, tramadol, viminol, xenbucin, zomepirac, and pharmaceutically acceptable salts thereof.

Local anesthetic agents include amucaine, amolanone, amylocaine hydrochloride, benoxinate, benzocaine, betoxycaine, biphenamine, bupivacaine, butacaine, butaben, butanilicaine, butethamine, butoxycaine, carticaine, chloroprocaine hydrochloride, cocaethylene, cocaine, cyclomethycaine, dibucaine hydrochloride, dimethisoquin, dimethocaine, diperadon hydrochloride, dyclonine, ecgonidine, ecgonine, ethyl chloride, betaeucaine, euprocin, fenalcomine, fomocaine, hexylcaine hydrochloride, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine hydrochloride, phenol, piperocaine, piridocaine, polidocanol, pramoxine, prilocaine, procaine, propanocaine, proparacaine, propipocaine, propoxycaine hydrochloride, pseudococaine, pyrrocaine, ropavacaine, salicyl alcohol, tetracaine hydrochloride, tolycaine, trimecaine, zolamine, and pharmaceutically acceptable salts thereof.

Antispasmodic agents include alibendol, ambucetamide, aminopromazine, apoatropine, bevonium methyl sulfate, bietamiverine, butaverine, butropium bromide, nbutylscopolammonium bromide, caroverine, cimetropium bromide, cinnamedrine, clebopride, coniine hydrobromide, coniine hydrochloride, cyclonium iodide, difemerine, diisopromine, dioxaphetyl butyrate, diponium bromide, drofenine, emepronium bromide, ethaverine, feclemine, fenalamide, fenoverine, fenpiprane, fenpiverinium bromide, fentonium bromide, flavoxate, flopropione, gluconic acid, guaiactamine, hydramitrazine, hymecromone, leiopyrrole, mebeverine, moxaverine, nafiverine, octamylamine, octaverine, oxybutynin chloride, pentapiperide, phenamacide hydrochloride, phloroglucinol, pinaverium bromide, piperilate, pipoxolan hydrochloride, pramiverin, prifinium bromide, properidine, propivane, propyromazine, prozapine, racefemine, rociverine, spasmolytol, stilonium iodide, sultroponium, tiemonium iodide, tiquizium bromide, tiropramide, trepibutone, tricromyl, trifolium, trimebutine, n,n-1 trimethyl-3,3-diphenyl-propylamine, tropenzile, trospium chloride, xenytropium bromide, and pharmaceutically acceptable salts thereof.

In certain embodiments, therapeutic agents for reducing pain or discomfort may be selected from ketorolac and pharmaceutically acceptable salts thereof (e.g., the tromethamine salt thereof, sold under the commercial name Torado®), 4-diethylamino-2-butynylphenylcyclohexylglycolate and pharmaceutically acceptable salts thereof (e.g., 4-diethylamino-2-butynylphenylcyclohexylglycolate hydrochloride, also known as oxybutynin chloride, sold under the commercial name Ditropang®), and combinations thereof. The amount of therapeutic agent present, will depend, for example, upon the efficacy of the therapeutic agent employed, the release rate, and so forth. One skilled in the art can readily determine an appropriate therapeutic agent loading to achieve the desired outcome.

In some embodiments, the surface of IB 115 is embossed with any of a variety of patterns. For example, in some embodiments the surface of IB 115 is embossed with a checkered pattern. Additionally, in some embodiments, inflatable balloon 115 tapers along its longitudinal direction.

In some embodiments, scoring wire 135 sits within SCW lumen 1139. And in some embodiments, SCW lumen 1139 sits outside of shaft 105.

Although the invention has been described in conjunction with specific embodiments, many alternatives, modifications, and variations will be apparent to those skilled in the art. Accordingly, it embraces all such alternatives, modifications, and variations that fall within the appended claims' spirit and scope. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A scoring balloon catheter comprising: a shaft; an inflatable balloon mounted at a distal region of the shaft;
   a handle mounted at a proximal region of the shaft;
   a hub including a spring, said hub mounted at the distal end of the handle with said spring coaxial with the shaft;
   at least one scoring wire having: a fixed distal end mounted on the shaft between a distal end of the shaft and the inflatable balloon;
   intermediate portions longitudinally tracing the outside of the balloon; and a proximal end welded to the spring; and
   a hub cover circumferentially surrounding at least a portion of the hub and the spring, said hub cover connected at a distal end to the shaft and at a proximal end to the handle.

2. The catheter of claim 1, wherein the proximal end of the scoring wire is welded to a distal portion of the spring such that the spring exerts a proximal force on the scoring wire.

3. The catheter of claim 1, wherein the hub at least partially surrounds the shaft.

4. The catheter of claim 1, wherein the hub at least partially surrounds the spring.

5. The catheter of claim 1, wherein the spring is biased against the hub.

6. The catheter of claim 1, wherein the hub connects to the handle and forms a monolithic structure.

7. The catheter of claim 1, wherein the spring at least partially surrounds the shaft.

8. The catheter of claim 1, further including an inflation lumen at least partially inside the shaft, the inflation lumen including a distal end inside the balloon.

9. The catheter of claim 1, further including a guidewire lumen at least partially inside the shaft.

10. The catheter of claim 9, wherein the handle includes a guidewire port connecting to a proximal end of the guidewire lumen.

11. The catheter of claim 8, wherein the handle includes a balloon inflation port connected to a proximal end of the inflation lumen.

12. A scoring balloon catheter comprising:
    a shaft;

an inflatable balloon mounted at a distal region of the shaft;

a hub mounted at a proximal region of the shaft;

a spring mounted to the hub with said spring coaxial with the shaft;

at least one scoring wire having: a fixed distal end mounted on the shaft between a distal end of the shaft and the inflatable balloon;

intermediate portions longitudinally tracing the outside of the balloon; and a proximal end welded to the spring; and a hub cover circumferentially surrounding at least a portion of the hub and the spring, said hub cover connected at a distal end to the shaft and at a proximal end to the hub.

13. The catheter of claim 12, wherein the spring is mounted at least partially within a recess in the hub.

\* \* \* \* \*